United States Patent [19]
Viets et al.

[11] Patent Number: 6,103,252
[45] Date of Patent: Aug. 15, 2000

[54] METHOD FOR REDUCING DEFLAGRATION OF AZINPHOS-METHYL

[75] Inventors: Alan K. Viets; Stephen W. Cohoon, both of Excelsior Springs, Mo.

[73] Assignee: Bayer Corporation, Pittsburgh, Pa.

[21] Appl. No.: 09/161,084

[22] Filed: Sep. 25, 1998

[51] Int. Cl.[7] ...................................................... A01N 25/18
[52] U.S. Cl. ............................ 424/405; 424/40; 424/489; 252/183.11; 252/183.12; 252/189; 252/190
[58] Field of Search ............................ 424/405, 40, 489; 252/183.11, 183.12, 189, 190

[56] References Cited

U.S. PATENT DOCUMENTS

| 3,585,022 | 6/1971 | Gray | 71/65 |
| 5,268,177 | 12/1993 | Barnett et al. | 424/405 |
| 5,622,658 | 4/1997 | Lloyd et al. | 264/15 |

FOREIGN PATENT DOCUMENTS

| 63-39803 | 2/1988 | Japan . |
| 1112778 | 5/1968 | United Kingdom . |

*Primary Examiner*—Richard L. Raymond
*Attorney, Agent, or Firm*—Joseph C. Gil; Carol Marmo

[57] ABSTRACT

The present invention relates to a stable azinphos-methyl wettable powder formulation. The composition of the present invention contains an insecticide powder formulation and a magnesium sulfate heptahydrate. The magnesium sulfate heptahydrate is added to the azinphos-methyl formulation in an amount such that the magnesium sulfate heptahydrate is from about 5% by weight to about 20% by weight of the total mixture. The addition of the magnesium sulfate heptahydrate reduces deflagration of the azinphos-methyl formulation and reduces the tendency of exothermic decomposition to occur.

8 Claims, No Drawings

METHOD FOR REDUCING DEFLAGRATION OF AZINPHOS-METHYL

BACKGROUND OF THE INVENTION

The present invention relates to an azinphos-methyl powder insecticide composition, and a process for preparing the composition, that reduces or eliminates the tendency of the azinphos-methyl composition to deflagrate and undergo exothermic decomposition.

Insecticides for open areas are generally applied by spraying. Sprays can be produced by either diluting liquid concentrates or by adding liquid to an insecticide in wettable powder form. The dry powder form of insecticides is generally preferred over the liquid form because it is less likely to penetrate the clothing and skin of the person handling it than a liquid concentrate. It is also easier to clean up a powder than a liquid in the event of a spill. However, azinphos-methyl in powder form is sensitive to heat. An ignition source could result in deflagration of the powder. As such, there is a need to make the powder forms of azinphos-methyl less likely to deflagrate without adversely affecting other desirable properties, such as storage stability.

A form of insecticides useful for treating enclosed, limited spaces is a fumigant. Japanese Patent 63,039,803 teaches an insecticide fumigant that undergoes controlled decomposition. In this fumigant, the insecticide is mixed with a thermodecomposable compound that will produce nitrogen and carbon dioxide at temperatures less than 300° C. Among the thermodecomposable compounds taught to be appropriate are ammonium salts, metal azides, inorganic carbonates and organic carboxylic acids. These thermodecomposable compounds are used in quantities such that they constitute at least 50% by weight of the fumigant mixture.

U.S. Pat. No. 5,268,177 teaches a process for raising the temperature at which deflagration of azinphos-methyl occurs by adding thereto a carbonate of alkali metal in an amount such that the carbonate is at least 10% by weight of the total mixture. The resultant mixtures are characterized by a reduced tendency toward deflagration at temperatures below 200° C. Examples 5 and 6 of Patent 5,268,177 illustrate comparative azinphos-methyl formulations in which magnesium sulfate and magnesium sulfate heptahydrate, respectively, were substituted for the carbonate or bicarbonate. The magnesium sulfate and the magnesium sulfate heptahydrate each constituted approximately 25% by weight of the azinphos-methyl formulations in Examples 5 and 6, respectively. Deflagration (manifested by smoke generation) of both the Example 5 and 6 formulations occurred at a temperature of 188° C.

SUMMARY OF THE INVENTION

It is an object of the present invention to provide a stable azinphosmethyl wettable powder composition, and a process for preparing the composition, that reduces or eliminates the tendency of the azinphosmethyl composition to deflagrate. By the term "stable" herein it is meant a physical and chemical stability of the azinphos-methyl composition that can manifest as follows (i) physically stable compositions retain their physical integrity (typically, physically stable compositions do not cake); and (ii) chemically stable compositions retain their active ingredient content over a period of time that can extend to several years.

This and other objects that will be apparent to those skilled in the art are accomplished by adding a magnesium sulfate heptahydrate to an azinphos-methyl formulation in an amount such that the magnesium sulfate heptahydrate is from about 5% by weight to about 20% by weight of the total mixture.

DETAILED DESCRIPTION OF THE PREFERRED EMBODIMENTS OF THE INVENTION

The composition and process of the present invention comprise a combination of an insecticide powder formulation and magnesium sulfate heptahydrate. The insecticide powder formulation includes azinphos-methyl as an active ingredient, known inert ingredients that are commonly used as carriers; and known materials commonly used to promote dispersibility of the azinphos-methyl in water. Suitable carriers include clays such as kaolin clay and attapulgite clay, amorphous silica, fumed silica, and hydrated silica. Suitable dispersibility agents include naphthalene sulfonates, lignosulfonates, and ethylene oxide/propylene oxide block polymers.

In the azinphos-methyl compositions of the invention, the magnesium sulfate heptahydrate is present in an amount such that it will constitute from about 5% by weight to about 20% by weight of the composition, and preferably from about 5% by weight to about 10% by weight of the composition. The azinphos-methyl is present in an amount such that it will constitute from about 50% by weight to about 65% by weight of the azinphos-methyl powder composition. In a preferred embodiment, about 50% by weight of the azinphos-methyl composition is the azinphos-methyl.

The wettable powder compositions of the present invention are characterized by a tendency to deflagrate that is significantly less than the tendency for deflagration of azinphos-methyl itself.

Having thus described the invention, the following examples are given as being illustrative thereof. All weights and percentages given are parts by weight or percentages by weight, unless otherwise indicated.

EXAMPLES

Example 1

Determination of Deflagration

Insecticide compositions (Examples 1 through 6) containing the ingredients listed in Table 1, in the relative amounts indicated in Table 1, were made by mixing the ingredients and then milling. Samples of each of the mixtures were filled in a vertically standing, closed bottom glass tube (inside diameter approximately 2.5 cm, height approximately 24 cm), up to approximately 6 cm below the upper edge, at room temperature. A soldering iron served as the ignition source. The soldering iron tip (1100° F.) was inserted into the insecticide composition for approximately one minute. If the material did not maintain a burn, after 8 minutes of inactivity, the tip was re-inserted into the composition for another minute. The results of the deflagration test for the compositions listed in Table 1, appear in Table 2. Example 6 is a comparative basic azinphos-methyl composition (Guthion 50 WP) to which a magnesium sulfate heptahydrate was not added.

TABLE 1

| | Example No. | | | | | |
|---|---|---|---|---|---|---|
| Ingredients (%) | 1 | 2 | 3 | 4 | 5 | 6* |
| Azinphos-Methyl | 54.0 | 54.0 | 54.0 | 54.0 | 54.0 | 54.0 |
| Sodium Diisopropyl | 3.0 | 3.0 | 3.0 | 3.0 | 3.0 | 3.0 |

TABLE 1-continued

| Ingredients (%) | Example No. | | | | | |
| --- | --- | --- | --- | --- | --- | --- |
| | 1 | 2 | 3 | 4 | 5 | 6* |
| Naphthalene Sulfonate Sodium Lignosulfonate | 3.0 | 3.0 | 3.0 | 3.0 | 3.0 | 3.0 |
| $MgSO_4 \cdot 7H_2O$ | 25.0 | 20.0 | 15.0 | 10.0 | 5.0 | — |
| Hydrated silica | 15.0 | 20.0 | 25.0 | 30.0 | 35.0 | 40.0 |

*Comparative formulation

TABLE 2

| Example No. | Sample Weight (grams) | Sample Height (cm.) | Exposure Time (min.) | Deflagration Comments |
| --- | --- | --- | --- | --- |
| 1 | 37.0 | 11.5 | 1 | did not burn |
| 2 | 27.4 | 11.5 | 1 | did not burn |
| 3 | 23.0 | 11.5 | 1 | did not burn |
| 4 | 21.4 | 11.5 | 1 | did not burn |
| 5 | 17.3 | 11.5 | 1 | did not burn |
| 6 | 14.5 | 12.5 | 1 | complete burn (2.42 g/min)* |

*In calculating the time for deflagration, the time was started when the soldering iron tip penetrated the glass tube inner seal, and time was ended when the smoke generation stopped.

The results in Table 2 show that the addition of the magnesium sulfate heptahydrate prevented deflagration of the azinphos-methyl powder compositions in Examples 1 through 5. The comparative composition of Example 6, without the magnesium sulfate heptahydrate, completely deflagrated.

The insecticide compositions of Examples 1 through 6 listed in Table 3, were prepared by mixing and then milling the ingredients listed in Table 1, in the relative amounts indicated in Table 1. The compositions were then stored for two week intervals at temperatures of 40° C. and 50° C. to evaluate their physical stability. The results of this physical stability test are shown in Table 3.

TABLE 3

| Example Number | 2 wks. @ 40° C. | 2 wks. @ 50° C. |
| --- | --- | --- |
| 1 | caked badly | caked badly |
| 2 | caked | caked badly |
| 3 | caked slightly | caked |
| 4 | no caking | caked slightly |
| 5 | no caking | no caking |
| 6 | no caking | no caking |

The results in Table 3 show that the composition of Example 1, containing 25% by weight of the magnesium sulfate heptahydrate, caked badly when stored for two weeks at both 40° C. and 50° C. The compositions containing 20% by weight or less of the magnesium sulfate heptahydrate experienced less caking when stored. The composition of Example 5, containing 5% by weight of the magnesium sulfate heptahydrate, did not cake when stored for two weeks at temperatures of 40° C. and 50° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a stable azinphos-methyl powder formulation wherein the tendency for deflagration and exothermic decomposition to occur is reduced or eliminated, comprising adding magnesium sulfate heptahydrate to the azinphos-methyl powder formulation in an amount such that from about 5% by weight to about 20% by weight of the total mixture is the magnesium sulfate heptahydrate.

2. The process of claim 1 wherein the magnesium sulfate heptahydrate is present in an amount of from about 5% by weight to about 10% by weight.

3. The process of claim 1 wherein azinphos-methyl is present in the azinphos-methyl powder formulation in an amount such that from about 50% to about 65% by weight of the total mixture is the azinphos-methyl.

4. The process of claim 3 wherein the azinphos-methyl is present in an amount of about 50% by weight.

5. A stable insecticide composition wherein the tendency to undergo deflagration and exothermic decomposition is reduced or eliminated, comprising a mixture of an azinphos-methyl powder and magnesium sulfate heptahydrate in which from about 5% by weight to about 20% by weight of the total mixture is the magnesium sulfate heptahydrate.

6. The composition of claim 5 wherein the magnesium sulfate heptahydrate is present in an amount of from about 5% by weight to about 10% by weight.

7. The composition of claim 5 wherein azinphos-methyl is present in the azinphos-methyl powder in an amount such that from about 50% to about 65% by weight of the total mixture is the azinphos-methyl.

8. The composition of claim 7 wherein the azinphos-methyl is present in an amount of 50% by weight.

* * * * *